United States Patent [19]

Ramanathan

[11] 4,083,688

[45] Apr. 11, 1978

[54] DISAZO PYRAZOLYL DYED POLYESTER FIBERS

[75] Inventor: Visvanathan Ramanathan, Basel, Switzerland

[73] Assignee: Ciba-Geigy AG, Basel, Switzerland

[21] Appl. No.: 410,747

[22] Filed: Oct. 29, 1973

Related U.S. Application Data

[63] Continuation-in-part of Ser. No. 191,535, Oct. 21, 1971, abandoned, which is a continuation-in-part of Ser. No. 816,394, Apr. 15, 1969, abandoned.

[30] Foreign Application Priority Data

Apr. 24, 1972 Switzerland .................... 6112/72

[51] Int. Cl.² ............... C09B 35/22; C09B 35/24; C09B 35/34; D06P 3/48
[52] U.S. Cl. ................................. 8/41 C; 260/154; 260/155; 260/156; 260/157; 260/158
[58] Field of Search .................... 260/160; 8/41 C

[56] References Cited

U.S. PATENT DOCUMENTS

| | | | |
|---|---|---|---|
| 2,936,306 | 5/1960 | Schmid et al. | 260/176 |
| 3,124,566 | 3/1964 | Jung et al. | 260/160 |
| 3,325,468 | 6/1967 | Jung et al. | 260/160 |

FOREIGN PATENT DOCUMENTS

| | | | |
|---|---|---|---|
| 885,851 | 6/1943 | France | 260/160 |
| 264,287 | 9/1913 | Germany. | |
| 393,592 | 11/1965 | Switzerland | 260/160 |

*Primary Examiner*—Floyd D. Higel
*Attorney, Agent, or Firm*—Edward McC. Roberts; Michael W. Glynn; Prabodh I. Almaula

[57] ABSTRACT

Polyester fibers dyed with a disazo dyestuff consisting of two N-phenyl-pyrazole monoazo dyestuff moieties bound to each other via the phenyl groups, said phenyl groups attached to each other by an —O—, —S—, —NH—, cyclohexylidene, $C_1$-$C_2$-alkylene or —O-($C_1$-$C_2$-alkylene)-O- divalent radical.

5 Claims, No Drawings

DISAZO PYRAZOLYL DYED POLYESTER FIBERS

CROSS-REFERENCE TO RELATED APPLICATION

This application is a continuation-in-part of application Ser. No. 191,535, filed Oct. 21, 1971, now abandoned; application Ser. No. 191,535 is in turn a continuation-in-part of application Ser. No. 816,394, filed Apr. 15, 1969; abandoned.

This invention provides new and valuable disazo dyestuffs of the formula

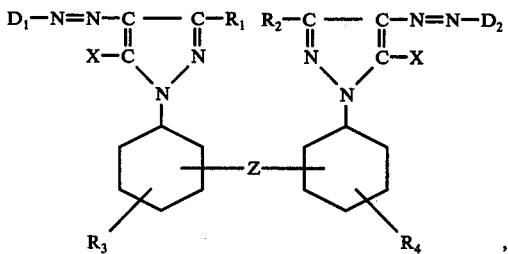

in which X represents a hydroxyl group or preferably an amino group, $R_1$ and $R_2$ each represents a hydrogen atom or an aryl residue, an alkoxy residue or especially an alkyl residue, and, when X = OH, also a carbalkoxy or carboxylic acid amide residue, $D_1$ and $D_2$ each represents a residue of a diazo component that may be quaternated, Z represents an oxygen or a sulphur atom or an organic residue which is free from oxygen atoms outside the chain, and $R_3$ and $R_4$ each represents an alkyl or alkoxy group or a halogen atom or especially a hydrogen atom.

The residues $R_1$ and $R_2$ can be, for example phenyl, ethoxy and especially methoxy and methyl groups, and, when X is a hydroxyl group, the residue $R_1$ and $R_2$ bound to the same pyrazole ring can also be a group of the formula —COOCH$_3$ or —COOC$_2$H$_5$ or a residue of the formula —CONH$_2$ that may be N-alkylated.

The diazo residues $D_1$ and $D_2$ are derived mainly from monocyclic or bicyclic amines of the formula

D-NH$_2$, for example, any diazotizable heterocyclic amine that does not contain acidic substituents imparting solubility in water, but especially from amines containing a five-membered ring having 2 or 3 hetero atoms, especially a nitrogen atom and one or two sulphur, oxygen or nitrogen atoms, and aminobenzenes, especially those of the formula

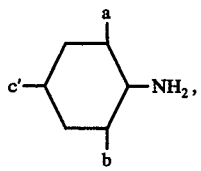

in which $a$ represents a hydrogen or a halogen atom or an alkyl, alkoxy, nitro, cyano, carbalkoxy or alkylsulphone group, $b$ represents a hydrogen or a halogen atom or an alkyl, cyano or trifluoromethyl group and $c'$ represents a nitro, cyano, carbalkoxy or alkylsulphonyl group.

The following are given as examples:- 2-aminothiazole, 2-amino-5-nitrothiazole, 2-amino-5-methylsulphonylthiazole, 2-amino-5-cyanothiazole, 2-amino-4-methyl-5-nitrothiazole, 2-amino-4-methylthiazole, 2-amino-4-phenylthiazole, 2-amino-4-(4'-chloro)-phenylthiazole, 2-amino-4-(4'-nitro)-phenylthiazole, 3-aminopyridine, 3-aminoquinoline, 3-aminopyrazole, 3-amino-1-phenylpyrazole, 3-aminoindazole, 3-amino-1,2,4-triazole, 5-(methyl-, ethyl-, phenyl- or benzyl-)-1,2,4-triazole, 3-amino-1-(4'-methoxyphenyl)-pyrazole, 2-aminobenzthiazole, 2-amino-6-methylbenzthiazole, 2-amino-6-methoxybenzthiazole, 2-amino-6-chlorobenzthiazole, 2-amino-6-cyanobenzthiazole, 2-amino-6-thiocyanogenbenzthiazole, 2-amino-6-nitrobenzthiazole, 2-amino-6-carboethoxybenzthiazole, 2-amino-(4- or 6-)-methylsulphonylbenzthiazole, 2-amino-1,3,4-thiadiazole, 2-amino-1,3,5-thiadiazole, 2-amino-4-phenyl- or -4-methyl-1,3,5-thiadiazole, 2-amino-5-phenyl-1,3,4-thiadiazole, 2-amino-3-nitro-5-methylsulphonylthiophene, 2-amino-3,5-bis-(methylsulphonyl)-thiophene, 5-amino-3-methylisothiazole, 2-amino-4-cyanopyrazole, 2-(4'-nitrophenyl)-3-amino-4-cyanopyrazole, 3- or 4-aminophthalimide, aminobenzene, 1-amino-4-chlorobenzene, 1-amino-4-bromobenzene, 1-amino-4-methylbenzene, 1-amino-4-nitrobenzene, 1-amino-4-cyanobenzene, 1-amino-2,5-dicyanobenzene, 1-amino-4-methylsulphonylbenzene, 1-amino-4-carbalkoxybenzene, 1-amino-2,4-dichlorobenzene, 1-amino-2,4-dibromobenzene, 1-amino-2-methyl-4-chlorobenzene, 1-amino-2-trifluoromethyl-4-chlorobenzene, 1-amino-2-cyano-4-chlorobenzene, 1-amino-2-carbomethoxy-4-chlorobenzene, 1-amino-2-carbomethoxy-4-nitrobenzene, 1-amino-2-chloro-4-cyanobenzene, 1-amino-2-chloro-4-nitrobenzene, 1-amino-2-bromo-4-nitrobenzene, 1-amino-2-chloro-4-carbethoxybenzene, 1-amino-2-chloro-4-methylsulphonylbenzene, 1-amino-2-methylsulphonyl-4-chlorobenzene, 1-amino-2-methylsulphonyl-4-nitrobenzene, 1-amino-2,4-dinitrobenzene, 1-amino-2,4-dicyanobenzene, 1-amino-2-cyano-4-methylsulphonylbenzene, 1-amino-2,6-dichloro-4-cyanobenzene, 1-amino-2,6-dichloro-4-nitrobenzene, 1-amino-2,4-dicyano-6-chlorobenzene, 4-aminobenzoic acid cyclohexylester, 1-amino-2,4-dinitro-6-chlorobenzene and especially 1-amino-2-cyano-4-nitrobenzene; also 1-aminobenzene-2-, -3-, or -4-sulphonic acid amides, for example N-methyl- or N,N-dimethyl- or diethyl-amide, and salts of ω-trimethylammoniumpara-aminoacetophenone, N,γ-isopropyloxypropyl-2-aminonaphthalene-6-sulphonic acid amide, N,γ-isopropyloxypropyl-1-aminobenzene-2-, -3- or -4-sulphonic acid amide, N-isopropyl-1-aminobenzene-2-, -3- or 4-sulphonic acid amide, N,γ-methoxypropyl-1-aminobenzene-2-, -3- or -4-sulphonic acid amide, N,N-bis-(β-hydroxyethyl)-1-aminobenzene-2-, -3- or -4-sulphonic acid amide, 1-amino-4-chlorobenzene-2-sulphonic acid amide, and the N-substituted derivatives, 2-, 3- or 4-aminophenylsulphamate, 2-amino-4-, -5- or -6-methylphenylsulphamate, 2-amino-5-methoxyphenylsulphamate, 3-amino-6-chlorophenylsulphamate, 3-amino-2,6-dichlorophenylsulphamate, 4-amino-2- or -3-methoxyphenylsulphamate, N,N-dimethyl-2-aminophenylsulphamate, N,N-di-n-butyl-2-aminophenylsulphamate, N,N-dimethyl-2-amino-4-chlorophenylsulphamate, N,n-propyl-3-aminophenylsulphamate, N,N-di-n-butyl-3-aminophenylsulphamate, 0-(3-aminophenyl)-N-morpholine-N-sulphonate, 0-(3-aminophenyl)-N-piperidine-sulphonate, N-cyclohexyl-0-(3-aminophenyl)-sulphamate, N-(N-methylaniline)-0-(3-aminophenyl)-sulphonate, N,N-diethyl-3-amino-6-methylphenyl-sulphamate, N-ethyleneimine-0-(4-aminophenyl)-sulphonate, N,N-dimethyl-4-aminophenylsulphamate, 0-(n-propyl-0-(3-aminophenyl)-sulphonate, 0β-chloroethyl-0-(2-aminophenyl)-sulphonate, 0-benzyl-0-(3-aminophenyl)-sulphonate, 0-ethyl-0-(4-amino-2,6-dimethylphenyl)-sulphonate, 4-aminoazobenzene, 3,2'-dimethyl-4-aminoazobenzene, 2-methyl-5-methoxy-4-aminoazobenzene, 4-amino-2-nitroazobenzene, 2,5-dimethoxy-4-aminoazobenzene, 4'-methoxy-4-aminoazobenzene, 2-methyl-4'-methoxy-4-aminoazobenzene, 3,6,4'-trimethoxy-4-aminoazobenzene, 4'-chloro-4-aminoazobenzene, 2'-or 3'-chloro-4-aminoazobenzene, 3-nitro-4-amino-2',4'-dichloroazobenzene and 4-aminoazobenzene-4'-sulphonic acid amide.

The above-mentioned diazo components which are free from ionic groups imparting solubility in water can be replaced by components containing fibre-reactive groups, for example, s-triazinyl residues containing one or two chlorine atoms or bromine atoms bound to the triazine ring, pyrimidyl residues containing one or two chlorine atoms or one or two arylsulphonyl or alkanesulphonyl groups bound to the pyrimidine ring, mono- or bis-(γ-halogeno-β-hydroxypropyl)-amino groups, β-halogenethylsulphamyl residues, β-halogenethoxy groups, β-halogenethylmercapto groups, 2-chlorobenzthiazolyl-6-azo groups, 2-chlorobenzthiazolyl-6-amino groups, γ-halogeno-β-hydroxypropylsulphamyl residues, chloroacetylamino groups, α,β-dibromopropionyl groups, vinylsulphonyl groups and 2,3-epoxypropyl groups.

Suitable fibre-reactive diazo components are, for example, N,β-chloroethyl-3-chloro-4-aminobenzenesulphamide (hydrochloride), N,β-chloroethyl-4-aminobenzenesulphamide (hydrochloride), 3-bromo-4-amino-ω-chloroacetophenone, N,γ-chloro-β-hydroxypropyl-4-aminobenzenesulphamide, N,β-chloroethyl-1-amino-4-naphthylsulphonamide, N,β-chloroethyl-1-amino-3,5-dichlorobenzenesulphamide and 4-(γ-chloro-β-hydroxypropoxy)aniline.

The diazo residues $D_1$ and $D_2$, insofar as they contain quaternatable nitrogen atoms, and also be quaternated.

The divalent bridging component Z can be, for example a sulphur atom, an —NH— group, a cyclohexylene residue or a stilbene residue or an alkylene residue that may be interrupted by oxygen atoms or especially a methylene group or an oxygen atom.

The residues $R_3$ and $R_4$ are preferably methyl, ethyl, methoxy or ethoxy groups or chlorine or hydrogen atoms.

Dyestuffs that are specially preferred are those corresponding to the formula

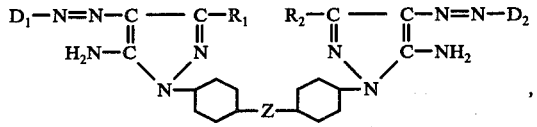

in which $D_1$ and $D_2$ each represents a monocyclic or bicyclic aromatic residue, $R_1$ and $R_2$ each represents a methyl or methoxy group and Z represents a residue of the formula —O— or —NH—.

The new dyestuffs may be obtained by coupling two mols of a diazonium compound of an amine of the formula $D_1$-$NH_2$ or $D_2$-$NH_2$, in which $D_1$ and $D_2$ have the meanings given above, with a coupling component of the formula

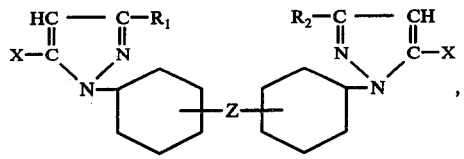

in which X, $R_1$, $R_2$ and Z have the meanings given above; when the residues $D_1$ and/or $D_2$ contain quaternatable nitrogen atoms, the dyestuffs obtained may be quaternated.

The preferred coupling components are compounds of the formula

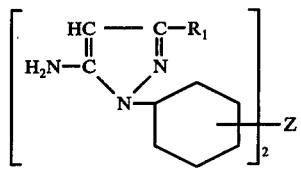

for example, bis-[4-methyl-3-(3'-methyl-5'-aminopyrazolyl-[1'])-phenyl]-methane or bis-[4-(3'-methyl-5'-aminopyrazolyl-[1'])-phenyl]-ether.

Some of these coupling components are new, and they may be obtained for example, by condensing two mols of cyanoacetone or cyanoacetone-imine with a bis-hydrazine of the formula

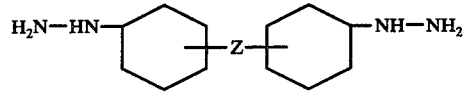

by known methods, preferably in aqueous solution acidified with a mineral acid.

Diazotization may be carried out by known methods for example, with an alkali metal salt of nitrous acid in an aqueous solution acidified with a mineral acid, or in concentrated sulphuric acid with nitrosylsulphuric acid.

Coupling may also be carried out in known manner, for example in a neutral to acid medium, if necessary, in the presence of sodium acetate or a similar buffer which influences the rate of coupling, or a catalyst, for example pyridine or a salt thereof.

After coupling, the non-quaternated dyestuffs that are formed can be isolated from the coupling mixture, for example by filtration, because they are practically insoluble in water.

Instead of a single diazo component a mixture of two or more diazo components may be used in accordance with the invention, and a single coupling component may be replaced by a mixture of two or more coupling components in accordance with the invention.

When the residues $D_1$ and/or $D_2$ of the diazo component contain quaternatable nitrogen atoms, for example, as in the case of the above-mentioned heterocyclic amines of the formulae $D_1$-$NH_2$ and $D_2$-$NH_2$, the dyestuffs can be quaternated, which process is preferably carried out as the last step.

Quaternation may be effected by a treatment with esters of strong mineral acids or organic sulphonic acids, for example dimethyl sulphate, diethyl sulphate, alkyl halides, for example methyl chloride, methyl bromide or methyl iodide, aralkyl halides, for example benzyl chloride, esters of low molecular weight alkanesulphonic acids, for example the methylester of methane-, ethane- or butane-sulphonic acid and the alkylesters of (4-methyl-, 4-chloro- or 3- or 4-nitro)-benzene sulphonic acid, which form as anions, for example halogen, sulphuric acid semi-ester, alkane or benzene sulphonic acid anions, preferably by heating in an inert organic solvent, for example xylene, carbon tetrachloride, ortho-dichlorobenzene and nitrobenzene. However, other solvents for example, acetic anhydride, dimethylformamide, acetonitrile or dimethylsulphoxide, can also be used. The quaternated dyestuffs preferably contain as anion $Y^-$ the residue of a strong acid, for example the residue of sulphuric acid or of a semi-ester thereof, or a halide ion, but they may also be used as double salts, for example with zinc chloride, or as free bases.

The dyestuffs described above are generally free from acidic groups imparting solubility in water, especially sulphonic acid groups, and are therefore either sparingly soluble or insoluble in water. However, they are soluble in water when they contain quaternated nitrogen atoms.

The new dyestuffs, mixtures thereof and mixtures of the new dyestuffs with other azo dyestuffs are eminently suitable for dyeing and printing synthetic fibres, for example acrylic or acrylonitrile fibres, polyacrylonitrile fibres and copolymers of acrylonitrile and other vinyl compounds, for example acrylic esters, acrylamides, vinylpyridine, vinyl chloride or vinylidene chloride, copolymers of dicyanoethylene and vinyl acetate and also of acrylonitrile block polymers, fibres made from polyurethanes, polyolefines, cellulose triacetate and secondary acetate, polyamides, for example nylon 6, nylon 66 and nylon 12, and especially fibres made from aromatic polyesters, for example fibres made from terephthalic acid and ethylene glycol or 1,4-dimethylolcyclohexane, and copolymers made from terephthalic and isophthalic acid and ethylene glycol.

This invention therefore also includes a process for dyeing or printing synthetic fibres, especially polyester fibres, wherein disazo dyestuffs are used which are free from carboxylic acid and sulphonic acid groups and which correspond to the formula

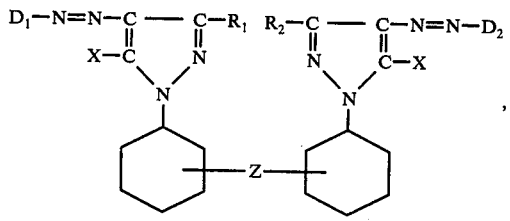

in which X represents a hydroxyl group or preferably an amino group, $R_1$ and $R_2$ each represents a hydrogen atom or an aryl residue, an alkoxy residue or especially an alkyl residue, and when X = OH, also a carbalkoxy or a carboxylic acid amide residue, $D_1$ and $D_2$ each represents a residue of a diazo component that may be quaternated and Z represents an organic residue that is free from oxygen atoms outside the chain.

Of particular interest are polyester fibers which have been dyed with a dyestuff free from $-SO_3H$ groups imparting solubility in water of the formula

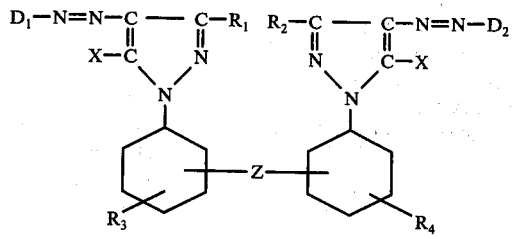

in which X represents hydroxyl or amino, $R_1$ and $R_2$ each represents hydrogen, phenyl, $C_1$-$C_2$-alkyl, $C_{1-2}$-alkoxy, and, when X = OH, also $C_1$-$C_2$-alkoxycarbonyl or —$CONH_2$, $D_1$ and $D_2$ each is a benzene group of the formula

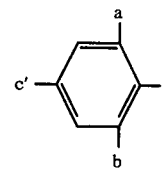

wherein $a$ is hydrogen, cyano, chloro, bromo, methyl, trifluoromethyl, carbomethoxy, methylsulfonyl, nitro, methoxy, ethoxy, sulfonic acid amide, N-$C_{1-3}$alkyl sulfonic acid amide, N-isopropyloxypropyl sulfonic acid amide or N,N-di-$C_{1-2}$alkyl sulfonic acid amide; $b$ is hydrogen or chloro; $c'$ is acetyl, ethylaminocarbonyl, nitro, cyano, methylsulfonyl, carb-$C_{1-2}$alkoxy, carbocyclohexyloxy, β-chloroethylaminosulfonyl, sulfonic acid amide, $C_{1-3}$alkyl sulfonic acid amide, N-isopropyloxypropyl sulfonic acid amide or N,N-di-$C_{1-2}$alkyl sulfonic acid amide; Z represents -O-, -S-, -NH-, cyclohexylidene, $C_1$-$C_2$-alkylene, -O-($C_1$-$C_2$-alkylene)-O-, and $R_3$ and $R_4$ each represent hydrogen, $C_1$-$C_2$-alkyl, $C_1$-$C_2$-alkoxy or chlorine.

The dyestuffs produce deep dyeings possessing good fastness to light and excellent fastness to sublimation.

Fibres containing ester groups, especially polyester fibres, may be dyed with the non-quaternated dyestuffs, which are preferably in a state of fine division, and dyeing is carried out in the presence of a dispersing agent, for example soap, sulphite cellulose waste liquor or a synthetic detergent, or a combination of different wetting and dispersing agents. Prior to dyeing, it is generally advantageous to convert the dyestuffs into dyeing preparations that contain a dispersing agent and finely divided dyestuff in a form such that a fine dispersion is formed on dilution with water. Such dyestuff preparations may be obtained in known manner, for example, by precipitating the dyestuff from sulphuric acid and grinding the suspension so obtained with sulphite cellulose waste liquor. If necessary, they may also be prepared by grinding the dyestuff in a highly efficient grinding device in the dry or wet state in the presence or absence of a dispersing agent.

By virtue of their fastness to alkali, the new water-insoluble dyestuffs are specially suitable for application by the so-called thermofixation process in which the material to be dyed is impregnated at a temperature not exceeding 60° C with an aqueous dispersion of the dyestuff which advantageously contains 1 to 50% of urea and a thickening agent, especially sodium alginate, and then squeezed in the usual manner. The impregnated material is advantageously squeezed so as to retain 50 to 100% of its dry weight of dye-liquor.

To fix the dyestuff, the material so impregnated is heated to a temperature above 100° C, for example to a temperature between 180° and 220° C, advantageously after drying, for example in a current of warm air.

Because of the high degree of fastness to sublimation which the new water-insoluble dyestuffs possess, textile materials dyed therewith can be subjected to a "permanent press" finish with thermosetting resins. The resins, together with latent hardeners, may be applied to the article after dyeing and then subjected to a hot curing treatment while the article is in the desired form.

The aforementioned thermofixation process is specially suitable for the dyeing of union fabrics made from polyester fibres and cellulosic fibres, especially cotton. In this case, in addition to the dispersed dyestuffs of the invention, the padding liquid contains dyestuffs suitable for dyeing cotton, especially vat dyestuffs or reactive dyestuffs, that is to say, dyestuffs capable of being fixed on the cellulosic fibre with formation of a chemical bond, for example, dyestuffs which contain a chlorotriazine or chlorodiazine residue. In the latter case, it is generally advantageous to add an agent capable of binding acid to the padding liquor, for example an alkali metal carbonate, an alkali metal phosphate, an alkali metal borate or an alkali metal perborate, or mixtures thereof. When using vat dyestuffs, the padded fabric must be treated after the heat treatment with an aqueous alkaline solution of one of the reducing agents commonly used in vat dyeing. The dyeings obtained are advantageously subjected to an aftertreatment, for example by heating with an aqueous solution of a non-ionic detergent.

By virtue of the fact that the water-insoluble dyestuffs of the invention reserve well on wool, they are eminently suitable for dyeing union fabrics made from polyester fibres and wool.

The water-insoluble dyestuffs may also be applied by printing processes. In this method of application a printing paste is used which contains, for example the finely divided dyestuff, the usual printing adjuvants, for example thickening and wetting agents, if necessary, in admixture with one of the above-mentioned cotton dyestuffs, with or without urea and/or an agent capable of binding acid. The dyestuffs can also be used for dyeing and printing in the form of solutions in organic media.

The new water-soluble quaternated dyestuffs or dyestuff salts are suitable for dyeing and printing a very wide variety of synthetic fibres, for example polyvinyl chloride, polyamide, polyurethane and especially polyacrylic fibres.

The new dyestuffs are also suitable for the bulk colouring of polymerization products of acrylonitrile, polyolefines and other synthetic materials; in this application they are added to the formulation prior to shaping. They are also suitable for colouring oil paints and lacquers.

Some of the new water-insoluble, non-quaternated products are valuable pigments that can be used for a wide variety of purposes. For example, they can be used in a state of fine division for the colouration of filament and staple-fibre viscose and cellulose ethers and esters, in the manufacture of inks, especially inks for ball-point pens, and in the manufacture of coloured lacquers and lake-formers, solutions and products made from cellulose acetate, nitrocellulose, natural and synthetic resins, for example, polymerization resins and condensation resins, for example aminoplasts, alkyd resins and phenoplasts and also polyolefines, for example polyethylene, polypropylene, polystyrene, polyvinyl chloride, polyacrylonitrile, rubber, casein, silicones and silicone resins.

The following Examples illustrate the invention, the parts and percentages being by weight, unless otherwise stated.

EXAMPLE 1

1.65 Parts of sodium nitrite are dissolved in 30 parts of sulphuric acid monohydrate. 3.6 Parts of 2-amino-5-nitrobenzonitrile are introduced at about 10° C, the mixture is stirred for 2 hours at 20° to 25° C and then discharged into 135 parts of ice-water. The diazo solution so obtained is added at 0° to 5° C to a solution of 3.86 parts of bis-[4-methyl-3-(3'-methyl-5'-aminopyrazolyl-[1'])-phenyl]-methane in a mixture of 150 parts of alcohol and a small amount of hydrochloric acid. The mixture is stirred for 10 hours. The dyestuffs which precipitates is isolated by filtration and washed with water until the washings run neutral. The dyestuff of the formula

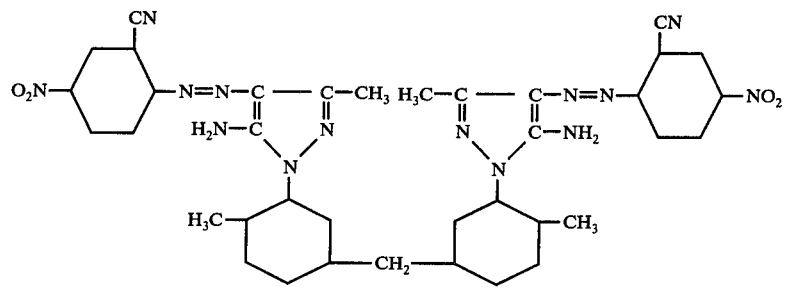

so obtained dyes polyester fibres an orange shade possessing excellent properties of fastness.

The coupling component may be obtained by reacting 1 mol of 4,4'-dimethyl-3,3'-bis-hydrazino-1,1'-diphenylmethane with 2 mols of diacetonitrile in aqueous solution acidified with hydrochloric acid.

Dyeing procedure:

1 Part of the dyestuff obtained in the manner described above is ground wet with 2 parts of a 50% aqueous solution of the sodium salt of dinaphthylmethane disulphonic acid, and the batch is then dried.

The dyestuff preparation so obtained is mixed with 40 parts of a 10% aqueous solution of the sodium salt of N-benzyl-μ-heptadecylbenzimidazole disulphonic acid and then 4 parts of 40% acetic acid solution are added. A dyebath of 4000 parts is prepared therefrom by dilution with water.

100 Parts of polyester fibre material, which has previously been cleaned, are entered into the dyebath at 50° C, the temperature is raised to 120 to 130° C within half an hour and dyeing is carried out for one hour at that temperature in a closed vessel. The material is then well rinsed.

EXAMPLE 2

1.65 Parts of sodium nitrite are strewn into 20 parts of concentrated sulphuric acid at 0° to 10° C. The mixture is heated at 65° C until all has dissolved. It is then cooled to 0° C and 22 parts by volume of a 4:1 mixture of glacial acetic acid and propionic acid are added dropwise. A solution of 3.2 parts of 2-amino-5-nitrothiazole in 22 parts by volume of a 4:1 mixture of glacial acetic acid and propionic acid is added dropwise to the solution so obtained, and the reaction mixture is stirred for 3 hours

EXAMPLE 3

3.9 Parts of 5-amino-3-phenyl-1,2,4-thiadiazole are dissolved in 22 parts by volume of formic acid. 1.55 Parts of sodium nitrite are introduced at 0° to 5° C and the batch is stirred for 30 minutes. 0.05 Part of sulphamic acid is then added. 3.58 Parts of bis-[3-(3'-methyl-5'-aminopyrazolyl-[1'])-phenyl]-methane are introduced and the mixture rinsed with 8 parts by volume of formic acid. The mixture is slowly heated to 60° C and then stirred at that temperature for 2 hours. The thick paste so obtained is diluted with 400 parts of water, well stirred, suction-filtered and the filter cake is washed with water. The dyestuff of the formula

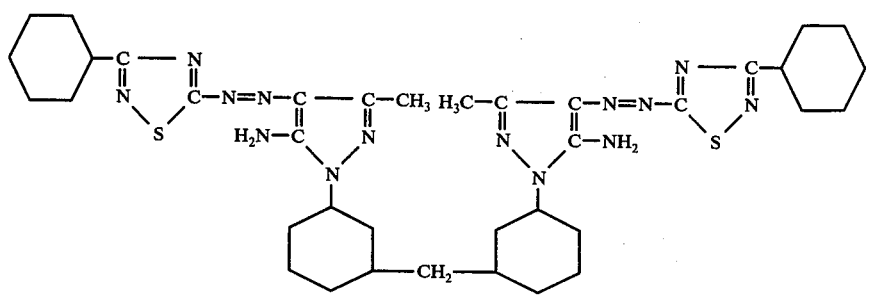

at 0° to 5° C. 1.65 Parts of urea are added in portions to the diazo solution so obtained. The diazo solution is added at 0° to 5° C to a solution of 3.6 parts of bis-[4-(3'-methyl-5'-aminopyrazolyl-[1'])-phenyl]-ether in 50 parts of alcohol. The mixture is stirred for about 10 hours and is then diluted with ice-water. The dyestuff which precipitates is isolated by filtration and washed with water until the washings run neutral. The dyestuff so obtained of the formula is obtained, which dyes polyester fibres a reddish yellow shade possessing very good properties of fastness.

The coupling component may be obtained from 3,3'-bis-hydrazinophenylmethane in a manner analogous to that described above.

The bis-hydrazines may be prepared from the corresponding diamines by diazotization and subsequent reduction with tin-(II) chloride.

The bis-aminopyrazol compounds indicated below

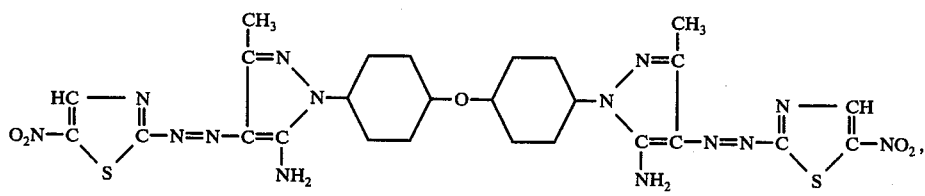

dyes polyester fibres a scarlet shade possessing excellent properties of fastness.

The coupling mixture may be obtained by reacting 4,4'-bis-hydrazino-1,1'-diphenylether with diacetonitrile in aqueous solution acidified with hydrochloric acid.

are obtained in an analogous manner.

By diazotizing the diazo component indicated in column I of the following Table in the manner described above and coupling with the coupling component indicated in column II, a dyestuff is obtained which dyes polyester fibres the shade shown in column III.

| | I | II | III |
|---|---|---|---|
| 1 | O$_2$N—⬡—NH$_2$ with CN | CH$_3$\C=N\ⁿ—⬡—O—⬡—N\N=C\CH$_3$ HC=C—NH$_2$ ... C=CH—NH$_2$ | orange |

-continued

| | I | II | III |
|---|---|---|---|
| 2 | 2,4-dinitro-6-chloro cyclohexylamine (NO₂, O₂N, Cl, NH₂) | " | red-orange |
| 3 | 2,4-dinitro cyclohexylamine | " | " |
| 4 | 2-chloro-4-nitro cyclohexylamine | " | golden yellow |
| 5 | 2-nitro cyclohexylamine | " | yellow |
| 6 | 4-nitro cyclohexylamine | " | " |
| 7 | 6-nitro-2-amino-hexahydrobenzothiazole | " | orange |
| 8 | 4-cyano cyclohexylamine | " | yellow |
| 9 | 2-chloro-4-methylsulfonyl cyclohexylamine | " | " |
| 10 | 2-cyclohexyl-5-amino-1,3,4-thiadiazole | " | " |
| 11 | 4-methoxycarbonyl cyclohexylamine | " | " |
| 12 | 2-trifluoromethyl-4-chloro cyclohexylamine | " | " |

-continued

| | I | II | III |
|---|---|---|---|
| 13 | 2-amino-5-nitrobenzonitrile (O₂N, CN, NH₂ on cyclohexane ring) | bis-coupler with -CH₂- bridge between two cyclohexane rings, each bearing -N(C(=CH)NH₂)(N=C(CH₃)-) | orange |
| 14 | 2-bromo-4-nitro aniline analog (O₂N, Br, NH₂) | " | golden yellow |
| 15 | 2-methoxy-4-nitro aniline analog (O₂N, OCH₃, NH₂) | " | " |
| 16 | 2-amino-5-nitrobenzonitrile (O₂N, CN, NH₂) | bis-coupler with -CH₂- bridge (meta-substituted rings) | orange |
| 17 | 2-amino-5-cyano-thiazole (NC-C=CH-N=C(NH₂)-S) | " | scarlet |
| 18 | 4-chloro-2-thio-methylidene-amino cyclohexane (Cl, S, N=C-NH₂) | " | orange |
| 19 | 2,4-dinitro aniline analog (NO₂, O₂N, NH₂) | bis-coupler with -CH₂- bridge, each ring bearing CH₃ substituent | reddish orange |
| 20 | 4-(N,N-dimethylsulfamoyl)aniline ((CH₃)₂NO₂S—, NH₂) | " | yellow |
| 21 | methyl 2-amino-5-nitrobenzoate (O₂N, COOCH₃, NH₂) | " | " |
| 22 | 5-nitro-2-amino thiazole (O₂N-C=CH-N=C(NH₂)-S) | " | scarlet |
| 23 | 4-cyano-2-thio-methylidene-amino cyclohexane (NC, S, N=C-NH₂) | " | orange |
| 24 | 2-cyclohexyl-5-amino-1,3,4-thiadiazole (cyclohexyl-C(N=N)C(NH₂)S) | " | yellow |

| | I | II | III |
|---|---|---|---|
| 25 | 4-nitrocyclohexylamine (O₂N–C₆H₁₀–NH₂) | bis[N-(2-chloro-5-methylene-cyclohexyl)-N-(1-methyl-ethylidene-amino)-aminoethene] bridged by CH₂ | " |
| 26 | 2-amino-5-nitro-cyclohexanecarbonitrile | corresponding bis-hydrazone with –CH₂CH₂– bridge | orange |
| 27 | " | corresponding bis-hydrazone with –OCH₂CH₂O– bridge | " |
| 28 | " | corresponding bis-hydrazone with –OCH₂–CH₂O– bridge (alternate) | " |
| 29 | " | corresponding bis-hydrazone with –S– bridge | " |
| 30 | " | corresponding bis-hydrazone, methyl-substituted cyclohexyl, bridged by C(CH₂CH₂)₂ (spiro) | " |
| 31 | " | corresponding bis-hydrazone, chloro-substituted cyclohexyl, bridged by C(CH₂CH₂)₂ (spiro) | " |
| 32 | " | bis[HC=N–N(CH=CH–NH₂)–cyclohexyl] bridged by –CH₂– | " |

| | I | II | III |
|---|---|---|---|
| 33 | " | (structure) | |
| 34 | " | (structure) | " |
| 35 | (structure) | | reddish orange |
| 36 | (structure) | (structure) | yellow (on polyester and nylon 6 in presence of alkali) |

EXAMPLE 4

3 Parts of 2-nitroaniline are triturated with 8 parts by volume of concentrated hydrochloric acid and diluted with 80 parts of ice and water. The suspension is diazotized by the addition of 5.5 parts by volume of a 4N sodium nitrite solution. The diazo solution so obtained is added to 0° to 5° C to a solution of 3.62 parts of bis-[4-(3'-methyl-5'-pyrazolonyl-[1'])-phenyl]-ether in 200 parts of alcohol. The mixture is rendered neutral to Congo paper with a sodium acetate solution and stirred for 12 hours. The dyestuff which precipitates is isolated by filtration and washed with water. The dyestuff so obtained which corresponds to the formula

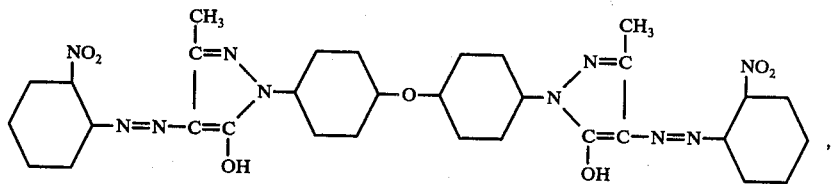

dyes polyester fibres a yellow shade possessing very good fastness properties.

The coupling component may be obtained by reacting 1 mol of 4,4'-bis-hydrazino-1,1'-diphenylether with 2 mols of acetoacetic acid ethyl ester.

The other bis-pyrazolones in the following Table may be prepared in an analogous manner. By diazotizing the diazo components listed in column I of the following Table and then coupling with the coupling components listed in column II, dyestuffs are obtained that dye polyester fibres the shades indicated in column III.

| | I | II | III |
|---|---|---|---|
| 1 | (structure) | (structure) | yellow |

-continued

| I | II | III |
|---|---|---|
| 2 ![structure] CH₃OOC—⌬—NH₂ | [bis-coupling structure with CH₃, HC=C-OH, CH₂ bridge] | " |
| 3 ![structure] CH₃O—⌬(NO₂)—NH₂ | [similar bis-coupling structure with CH₃ groups on rings] | orange |
| 4 ![structure] O₂N—⌬(Cl)—NH₂ | " | yellow |
| 5 ![structure] O₂N—⌬—NH₂ | [bis-coupling structure with COOC₂H₅, CH₃, HC=C-OH, CH₂ bridge] | " |
| 6 ![structure] O₂N—⌬(Cl)—NH₂ | " | " |

EXAMPLE 5

5 Parts of 4-aminophenacyltrimethylammonium chloride are dissolved in 25 parts of water and then 8 parts by volume of concentrated hydrochloric acid are added. The solution is diazotized at 0° to 5° C by the addition of 5.5 parts by volume of 4N sodium nitrite solution. The diazo solution is added at 0° to 5° C to a solution of 3.58 parts of bis-[4-(3'-methyl-5'-aminopyrazolyl)-[1']-phenyl]-methane in 40 parts of water and 2.5 parts of concentrated hydrochloric acid. The coupling mixture is rendered neutral to Congo paper by the addition of a sodium acetate solution. After coupling, the dyestuff is precipitated by the addition of salt. The dyestuff is isolated by filtration, dissolved in hot water, the solution is filtered and the dyestuff is salted out of the filtrate. The dyestuff which precipitates corresponds to the formula

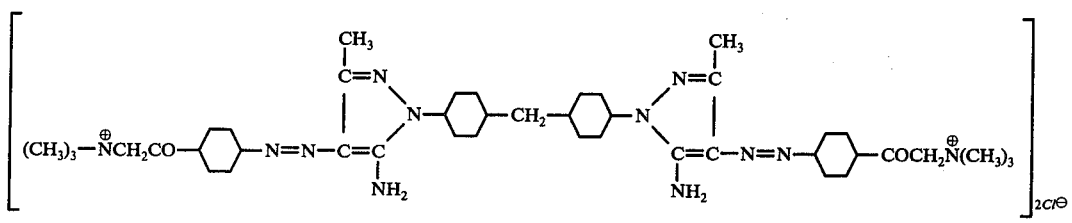

It is isolated by filtration and dried. The dyestuff so obtained dyes polyacrylonitrile fibres a yellow shade possessing excellent properties of fastness.

By diazotizing the diazo components listed in column I of the following Table and then coupling with the coupling components listed in column II, dyestuffs are obtained that dye polyacrylonitrile fibres the shades listed in column III.

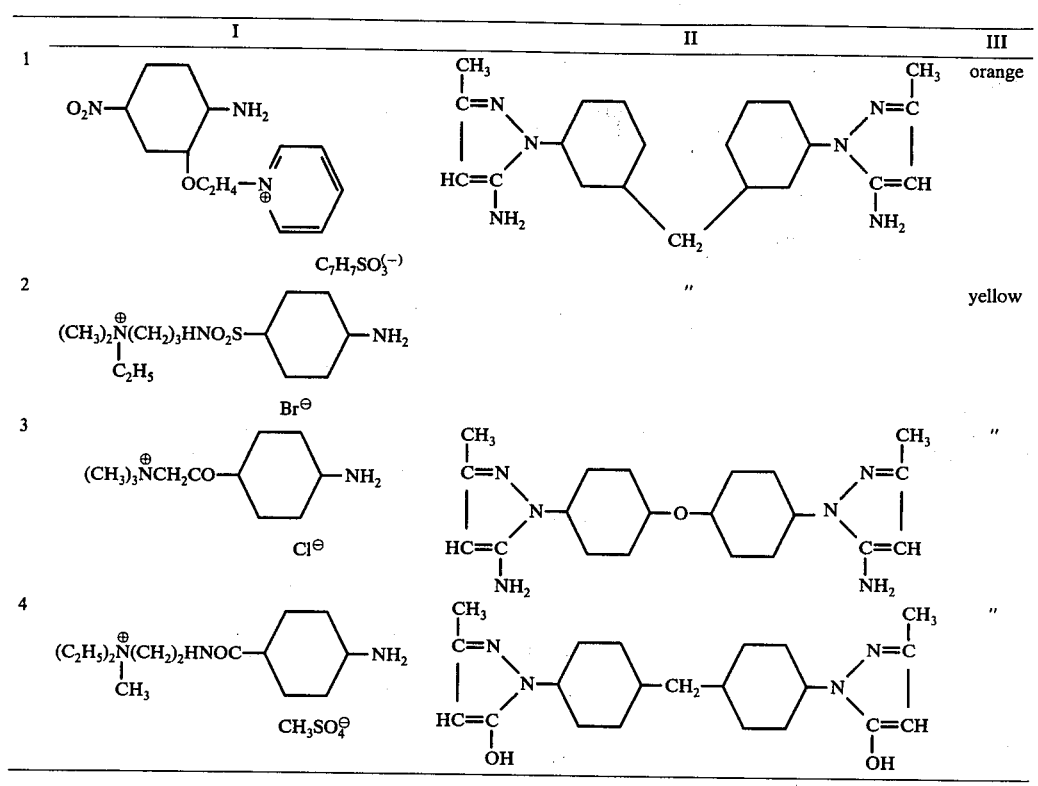

EXAMPLE 6

4.14 parts of 3-aminopyridine are dissolved in 150 parts of water and 17.6 parts by volume of concentrated hydrochloric acid. The solution is diazotized at 0° to 5° C by the addition of 11 parts of volume of a 4N sodium nitrite solution. The diazo solution is added at 0° to 5° C to a solution of 3.58 parts of bis-[4-(3′-methyl-5′-aminopyrazolyl)-[1′]-phenyl)-methane in 40 parts of water and 2.5 parts of concentrated hydrochloric acid. After coupling, the pH of the coupling mixture is adjusted to 7 – 8 by the addition of sodium hydroxide solution. The dyestuff is isolated by filtration, washed with water and dried.

5.68 Parts of the dyestuff so obtained are dissolved hot in 150 parts of chlorobenzene. 3.9 Parts of dimethyl sulphate dissolved in 20 parts of chlorobenzene are added dropwise and the reaction mixture is stirred for 3 hours at 95° to 100° C. After cooling, the solution is filtered, the filter residue is dissolved in hot water, the solution is filtered and then the dyestuff is salted out of the filtrate. The dyestuff of the formula

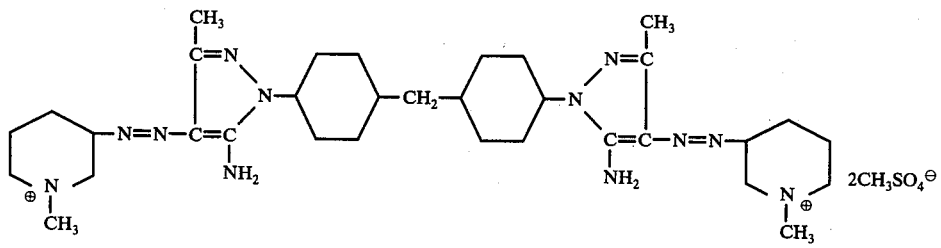

so obtained is isolated by filtration and dried. It dyes polyacrylonitrile fibres a yellow shade possessing very good properties of fastness.

By diazotizing the diazo components listed in column I of the following Table and coupling with the coupling components listed in column II, and then alkylating the product obtained with the alkylating agent indicated in column III, dyestuffs are obtained that dye polyacrylonitrile fibres the shades listed in column IV.

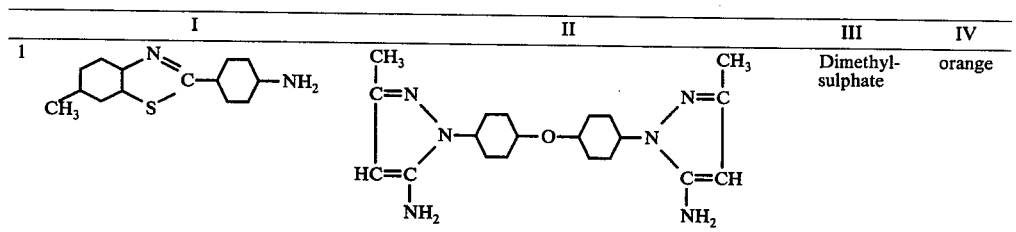

-continued

| | I | II | III | IV |
|---|---|---|---|---|
| 2 | 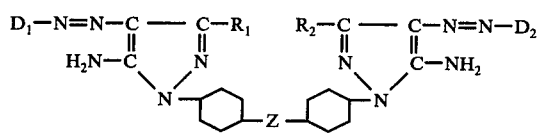 | | Dimethyl-sulphate | yellow-brown |

I claim:

1. Polyester fiber dyed with a disazo disperse dyestuff, free from —SO₃H groups impartingg solubility in water, and having the formula $$D_1-N=N-C\underset{H_2N-C}{\overset{\|}{C}}-\underset{N}{\overset{\|}{C}}-R_1 \quad R_2-\underset{N}{\overset{\|}{C}}-\underset{C-NH_2}{\overset{\|}{C}}-N=N-D_2$$

wherein
Z is —O— or —NH-;
R₁ and R₂ each represent methyl or methoxy; and
D₁ and D₂ each is a group of the formula

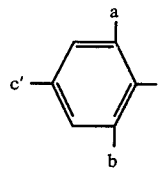

wherein a is hydrogen, cyano, chloro, bromo, methyl, trifluoromethyl, carboxymethoxy, methylsulfonyl, nitro, methoxy, ethoxy, sulfonic acid amide, N-C$_{1-3}$ alkyl sulfonic acid amide, N-isopropyloxypropyl sulfonic acid amide or N,N-di-C$_{1-2}$alkylsulfonic acid amide; b is hydrogen, bromo or chloro; c' is C$_{1-2}$ -alkylcarbonyl, C$_{1-2}$-alkylaminocarbonyl, nitro, cyano C$_{1-2}$- alkylsulfonyl, carbo-C$_{1-2}$alkoxy, carbocyclohexyloxy, β-chloroethylaminosulfonyl, sulfonic acid amide, N-C$_{1-3}$alkyl sulfonic acid amide, N-isopropyloxypropyl sulfonic acid amide or N,N-di-C$_{1-2}$-alkyl sulfonic acid amide.

2. Polyester fiber according to claim 1, wherein a dyestuff is used wherein c' is nitro, cyano, C$_1$-C$_2$-alkylsulphonyl, C$_1$-C$_2$-alkylaminosulphonyl, di-(C$_1$-C$_2$-alkyl)aminosulphonyl, C$_1$-C$_2$-alkyloxycarbonyl or C$_1$-C$_2$-alkylcarbonyl.

3. Polyester fiber according to claim 1 which is dyed with a dyestuff wherein a is hydrogen, chlorine, bromine, methyl, methoxy, nitro, cyano, carbo-C$_1$-C$_2$-alkoxy or methylsulphonyl, b is hydrogen, methyl, bromine, chlorine, cyano or trifluoromethyl and c' is nitro, cyano, carbo-C$_{1-2}$alkoxy or methylsulphonyl.

4. The composition according to claim 1 wherein the polyester fibre is selected from the group consisting of the polyester of terephthalic acid and ethylene glycol; the polyester of terephthalic acid and 1,4-dimethylolcyclohexane; and the polyester copolymer of terephthalic and isophthalic acid and ethylene glycol.

5. Polyester fiber which is dyed with a dyestuff of the formula

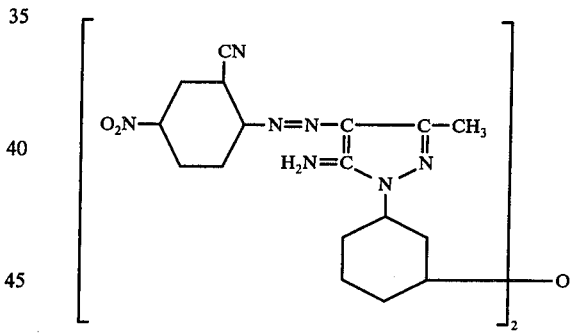

* * * * *